United States Patent [19]

Pang et al.

[11] 4,230,684

[45] Oct. 28, 1980

[54] METHOD FOR DETERMINING STEROIDS IN HUMAN BODY LIQUIDS

[75] Inventors: Songja Pang; Maria I. New, both of New York, N.Y.

[73] Assignee: Cornell Research Foundation, Inc., Ithaca, N.Y.

[21] Appl. No.: 887,326

[22] Filed: Mar. 16, 1978

[51] Int. Cl.$^2$ .................. A61K 43/00; G01N 33/16; B65D 81/32

[52] U.S. Cl. ............................. 424/1; 424/12; 23/230 B; 23/230.6; 422/61

[58] Field of Search ............... 424/6, 12; 23/230 B, 23/230.6; 422/61

[56] References Cited

U.S. PATENT DOCUMENTS

| | | | |
|---|---|---|---|
| 4,018,885 | 4/1977 | Bohn et al. | 424/12 |
| 4,081,525 | 3/1978 | Knight et al. | 424/1 |

OTHER PUBLICATIONS

James, In Radioimmuno Assay of Steroid Hormones, Ed. Gopta., Verlag Chemie, Weinheim, 1975, pp. 1-8.
Bruno, In New Techniques in Tumor Location and Radioimmuno Assay, Ed. Crollgtal, J. Wiley & Sons, Inc., N.Y., 1974, pp. 9-15.

*Primary Examiner*—Brooks H. Hunt
*Assistant Examiner*—Christine M. Nucker
*Attorney, Agent, or Firm*—Schwartz, Jeffery, Schwaab, Mack, Blumenthal & Koch

[57] ABSTRACT

A micromethod for the determination of steroids in human body liquids, in particular blood, is disclosed. A small sample of the liquid is transferred to a sheet of absorbing material, e.g., filter paper. A disc of the impregnated paper, containing the dried sample, in eluted with an aqueous solvent, e.g., a buffer solution. Without separating the paper from the elute, the latter is extracted with an organic solvent. A steroid-containing residue is recovered from the organic extract and is subjected to a conventional radioimmunoassay. The method is particularly suited for the detection of disorders with elevated steroid levels such as congenital adrenal hyperplasia in newborn infants by determining the 17α-hydroxy-progesterone concentration in small blood samples.

16 Claims, No Drawings

METHOD FOR DETERMINING STEROIDS IN HUMAN BODY LIQUIDS The invention described herein was made in the course of work under a grant from the Department of Health, Education and Welfare. Grant No. R01 HD00072.

BACKGROUND OF THE INVENTION

The present invention relates to a micromethod and means for the determination of steroids, in particular of 17α-hydroxy-progesterone, in human body liquids and to a new method and means for detection of congenital adrenal hyperplasia (CAH) in newborn humans.

CAH is an inborn error of metabolism which is transmitted by an autosomal recessive gene. This disorder is due to a 21-hydroxylase deficiency and is recognizable by a markedly increased blood level of 17α-hydroxy-progesterone.

The estimated incidence of congenital adrenal hyperplasia (CAH) based on different population groups indicates that CAH may occur in one out of every 11,000 live births. Failure of early diagnosis of CAH in the affected newborn may lead to life-threatening adrenal crises during the first few months of life, and in the genetic female there may be a need for sex reassignment if the ambiguity of the external genitalia has led to an incorrect sex assignment.

Furthermore, delayed diagnosis is almost always associated with the acceleration of skeletal maturation ultimately leading to short stature and premature development of secondary sex characteristics in male children and further virilization in female affected children. In view of the described known complications of the unrecognized and untreated disease, and in view of the relatively high frequency of the gene, as reflected in incidence, diagnostic delay is a serious problem.

A rapid screening program for the diagnosis of CAH during the newborn period is therefore desirable.

Until now measurements of urinary 17-ketosteroids and pregnanetriol in the 24-hour urine, and the determination of serum adrenal precursor hormone or androgen hormone have been used as diagnostic tests. In the normal infant, urinary 17-ketosteroid excretion is usually slightly increased during the newborn period. However, pregnanetriol in normal infants and infants with CAH, may not be elevated in urine. Therefore, these tests may not be diagnostic of CAH during the first few days of life. More recently, radioimmunoassay for the measurement of 17α-OH-progesterone has become available. The usefulness of this assay for the diagnosis of CAH has been well established (see, e.g., Youssefnejadian et al, Clin. Endocrinol. 4; 451, 1975, I. A. Hughes et al, J Pediatr 88: 766, 1976; and B. M. Lippe et al, J Pediatr 85: 782, 1974). However, all the prior art methods for the determination of steroids involve the analysis of blood plasma and require relatively large amounts of blood for the separation of the blood cell mass from the plasma. Further, sample collection by veno puncture is inconvenient in small infants.

In the recently developed radioimmunoassays, radiological means are employed to detect and/or measure the presence of a steroid in the patient's blood (or urine). In these radioimmunoassay tests, a solution of an antibody of the steroid is placed in contact with a mixture of the steroid, which has been extracted from a sample of the patient's body fluid to be tested and a known amount of the same steroid tagged with a radioactive isotope. The steroid in the test sample and the labeled steroid compete for interaction with the steroid antibody. The resulting steroids-antibody-complex is then separated from the fluid and either fraction may be analyzed radiologically in order to determine the respective proportions of the labeled and unlabeled steroid which became bound to the antibody. The concentration of steroid in the sample can be calculated from this information, since the proportion of labeled and unlabeled steroid will be in the same proportion in both fractions. The radioimmunoassay techniques exhibit a high degree of accuracy and specificity. Yet, like other prior art methods for steroid determination, the radioimmunoassay techniques also require relatively large amounts of blood for the preliminary separation of blood plasma from the hematocrit, and also have the usual disadvantage that samples can be stored only at low temperature, since the liquid samples are easily infected and spoiled by growth of bacteria.

SUMMARY OF THE INVENTION

It is an object of the present invention to provide a method for the determination of steroid hormones, in particular adrenal and gonadal sex steroids and corticosteroids, in small samples of human body liquids collected on a sample absorbing sheet (eg; filter paper), in particular, small blood samples, which avoids the disadvantages of the prior art methods.

It is an especial object of the present invention, to provide such a method which can be rapidly performed and requires only minute amounts of blood which can be easily obtained, e.g., from the finger tip or with heel prick in small children.

It is a further object of the present invention to provide such a method for determining the 17α-hydroxy-progesterone blood level of newborn infants.

It is a further object of the present invention to provide such a method, wherein the blood sample can easily be obtained by a practicing physician and then be mailed to steroid laboratories in medical centers, obviating the need for frozen storage, centrifugation, and special containers.

It is a further object of the present invention to provide a method for the determination of steroids in human body liquids, which is especially suited for surveying ambulatory patients.

Another object of the present invention resides in the provisions of a method for rapid and early diagnosis of CAH in newborn infants.

It is a further object of the present invention to provide such a diagnostic method, which is suitable for large scale screening for CAH in the newborn.

In order to accomplish the foregoing objects according to the present invention, there is provided a method for determination of a steroid in a sample of a human body liquid, which comprises the steps of:

(a) transferring said liquid sample onto a sheet of material (eg; filter paper) which is capable of uniformly absorbing said liquid sample;

(b) drying the sample-containing sheet;

(c) treating a portion of the dry sample-containing sheet, which is equivalent to a predetermined amount of the sample with an aqueous solvent in order to obtain a mixture wherein the dried blood is substantially redissolved in the aqueous solvent;

(d) extracting said aqueous mixture with a volatile organic solvent in order to obtain an organic extract, containing said steroid dissolved therein;
(e) separating at least a portion of said organic extract from said aqueous mixture;
(f) recovering a residue containing the steroid from said organic extract;
(g) contacting said residue with an aqueous solution of an agent, capable of selectively binding said steroid in the presence of a radio-isotopically labeled steroid, whereby part of said labeled steroid and part of said unlabeled steroid, present in the sample, are bound by forming a complex with said binding agent. Following this step said bound steroids are separated from unbound steroids in said aqueous solution and the radioactivity of at least said separated binding agent-steroids-complex or said unbound steroids is measured to determine the concentration of said hormone as a function of the measured radioactivity.

The above method is especially suitable for determining the concentration of adrenal and gonadal sex steroids and corticosteroids in small blood samples, especially 17α-hydroxy-progesterone. In addition to 17α-hydroxy-progesterone, examples of steroids which can readily be determined in the samples of whole blood according to the present method, are androstenedione, testosterone, dehydroepiandrosterone, dehydroepiandrosterone-sulfate and cortisol.

The steroid-binding agent, which is employed in the method according to the present invention, for determining steroids in human body fluids, may be any reagent conventionally employed in immuno chemical methods, in particular antisera for the respective steroids which are conventionally used in radioimmunoassays. The preparation of antisera for the various steroid hormones is well known in the art and these antisera are commercially available. In applying this method for the determination of 17α-hydroxy-progesterone in blood samples, the conventional antiserum for 17α-hydroxy-progesterone is used.

The radioisotopically labeled steroid, which is used as an indicating means, may comprise different radioactive isotopes, e.g., $^3H$ or $^{14}c$. For measuring the radioactivity, a conventional liquid scintillation counter, which is adapted for beta-counting, can be used.

In a preferred embodiment of the present invention, the 17α-hydroxy-progesterone content of a blood sample is determined by the following steps, 1; evaporating the organic solvent from the organic extract, which is obtained from the eluate of the blood sample, 2; adding an aqueous solution of a predetermined amount of an antiserum for 17α-hydroxy-progesterone to the resulting residue of step 1 and an aqueous solution which contains a predetermined amount of a radio-isotopically labeled form of 17α-hydroxy-progesterone, (which is in excess of the amount) which is required to bind said amount of antiserum, 3; allowing a steroid-radioactive steroid-antiserum-complex to form in the aqueous solution, 4; separating the unbound portions of the steroids from the aqueous solution, 5; determining the radioactivity of the remaining aqueous solution.

The method for determining steroids according to the present invention, using only extremely small amounts of human body liquids, is especially suited for detecting unduly high amounts of steroid hormones in the human body and provides a simple means for detecting disorders in the body functions which are characterized by increased levels of steroids in the body, for example, disorders of sexual ambiguity, salt-losing conditions, and disorders of puberty etc.

The method for determining 17α-hydroxy-progesterone in a small blood sample according to the present invention, is particularly suitable for detecting congenital adrenal hyperplasia (CAH) in newborn humans.

Accordingly, there is further provided, according to the present invention, a method for detecting congenital adrenal hyperplasia in newborn infants, which comprises the steps of collecting a small blood sample from the newborn infant and subjecting this blood sample to the above described method for determining the 17α-hydroxy-progesterone content therein.

Further objects, features, and advantages of the present invention will become apparent from the detailed description of the invention and its preferred embodiments, which follows:

DETAILED DESCRIPTION OF THE INVENTION

In accordance with the present invention, there has been discovered a novel micromethod for determining the concentration of specific steroids in human body liquids, in particular, in small samples of whole blood. According to the present invention, a small amount of a human body liquid, in particular human whole blood, is collected on a sheet of absorbing material, preferably a standard filter paper, from which the steroid can later be eluted. The amount of steroid, which is recovered from the eluate, is then determined in a conventional radioimmunoassay. The method of applying a small blood sample on a filter paper is a standard hospital procedure in the screening for phenylketonurea in newborns and has also been used for screening neonates for hypothyroidism (see Larsen et al, Pediatr. Res. 9, 604, 1975). Yet, such a method of collecting a blood sample on a filter paper with subsequent elution of the blood from the filter paper, has never been used in connection with the process of extracting a steroid-containing fraction from blood samples and measurements of the steroid-content by radioimmunoassay.

It has now been found that the steroid content in a whole blood sample, which has been absorbed and dried on an absorbing paper remains unchanged even if the blood-containing paper is stored at room temperature for a period of up to about one month. Even after such a long period of storage, the steroid-content of the blood sample can be completely recovered from the absorbing paper by elution of the dried blood-containing paper with an aqueous solution and subsequent extraction of the eluate with an organic solvent, which preferably is non-water-miscible. For example, an excellent correlation has been found between the values of 17α-hydroxy-progesterone, obtained from blood samples of newborn infants, which were treated by a microfilter-paper-method according to the present invention, and the values from plasma samples of cord- and neonatal blood samples, which were treated in a conventional procedure for radioimmunoassay tests in these infants.

The present invention exhibits several important advantages as compared with determinations of steroids by prior art: the minute amount of blood which is required, makes the method particularly suitable for detecting steroid disorders in the newborn, e.g., CAH. In addition, blood samples on filter paper can easily be sent by surface mail by physicians practicing in geographically isolated areas to steroid laboratories in Medi al Centers, obviating the need for frozen storage, centrifugation, and special containers. The method is suitable for the survey of ambulatory patients. In such situations, the family doctor could easily screen for a number of conditions and disorders, particularly, for excessive steroid production, e.g. in pregnancy, virilism of all kinds, Cushings syndrome, and possibly some adrenal and pituitary steroid deficient states. The presently claimed method is easy and rapid and has the specificity, accuracy, and precision of radioimmunoassays in whole plasma. The minute amount of blood which is required, the simplicity of sample collection which can be easily performed by heel prick, and the ease with which samples may be transported, make this method highly useful for large scale screenings. The presently claimed method is particularly valuable in screening programs for CAH in newborn infants. With the method according to the present invention, early screening for the CAH-disease in the majority of newborn infants by analysis of filter paper, which is impregnated with a small blood sample of newborn infants, is made possible. The collection of a small spot of blood on filter paper presents no hazards or difficulties to the newborn and provides the potential benefit of early diagnosis of CAH with a high degree of accuracy.

Summarizing the foregoing, the micromethod, according to the present invention, using samples of whole dried blood in an absorbing paper, is superior to the serum hormone assays in the following ways:
i. the minute amounts of blood required by the method;
ii. the simplicity of sample collection, by either medical or non-medical personnel;
iii. absence of risk of accidental loss of samples by breakage of glass tubing;
iv. absence of need to centrifuge blood samples;
v. convenience of sample delivery by surface or air mail in an envelope;
vi. convenience of sample storage;
vii. practical application of this method for the measurement of specific steroids in mass screening programs.

For transferring the blood sample to the absorbing material according to the present invention, a blood sample can be collected directly onto a sheet of absorbing material from a small cut, for example, in the finger tip of a patient or by means of heel prick from a newborn infant. Of course, a small portion of a larger blood sample, which has been drawn from a human being directly into a heparinized tube in a conventional manner, can also be transferred onto an absorbing sheet to be used in the present test method.

The necessary amount of body liquid, in particular blood, which is used in the present test method, of course, varies, depending on the respective steroid which is to be tested, the sensitivity of the antiserum which is available for this steroid and the condition of the patient to be diagnosed, e.g., the expected level of the steroid in the body liquid of the patient. For example, to detect an abnormally increased level of $17\alpha$-hydroxy-progesterone in blood, an amount of from about 10 to about 20 $\mu l$ is preferably used. The absorbing material is preferably a uniformly absorbing filter paper. Example of suitably absorbing papers are filter paper No. 903 of Schleicher and Schuell or the standard absorbing paper which is used for collecting blood samples in the hospital as a standard procedure for neonatal screening for phenylketonurea. Such filter paper can absorb only a certain amount of liquid per surface area unit. When the body liquid, e.g. blood, is dropped gently on the filter paper, a standard size of filter paper disc will contain a standard amount of the liquid. Therefore, an identical volume of test samples of the body liquid, e.g., the blood, in various tests, can be insured by using some kind of absorbing paper and punching out a standard size disc of the dry blood-containing absorbing paper for the recovery of the steroid therefrom. It has been found, that the steroids are uniformly distributed throughout the paper area, which has been impregnated with the body liquid, e.g., the blood.

For eluting the steroid from filter paper containing dried whole blood, the latter is treated with an aqueous eluant. Water or aqueous salt solutions may be used as eluants. The eluant preferably is an aqueous buffer solution, having a pH-value of from about 6 to about 8, e.g., a sodium monophosphate/sodium diphosphate buffer solution. In order to effectively elute whole amount of blood sample impregnated with absorbing sheet, the elution preferably takes place at a temperature at 25° C., which is sufficiently low not to cause substantial evaporation of the organic solvent during the subsequent extraction. Suitably the elution is carried out at a temperature of between about 15 and about 30° C., preferably at ambient temperature, preferably for a period of between about 15 and 30 minutes. Subsequently, an organic solvent is added without previously separating the absorbing paper from the eluate. The organic solvent is thoroughly mixed with the aqueous phase, e.g., by shaking the mixture by means of vibrating shakers, in order to extract the steroid therefrom.

The organic solvent preferably is a solvent which is non-miscible with the aqueous phase or is a solvent which precipitates those components of the aqueous solution, which may interfere with the later radioimmunoassay for the determination of the steroid. Examples of suitable nonwater-miscible solvents are ethers, such as diethylether, halogenated hydrocarbons, such as methylene chloride or chloroform, aromatic hydrocarbons, such as benzene aliphatic hydrocarbons, such as petrolether or hexane and mixtures thereof. Lower alkyl alcohols may serve as precipitating solvents. The choice of the most suitable solvent will, of course, depend on the properties of the steroid which is to be determined. In case of $17\alpha$-hydroxy-progesterone, diethyl ether is preferably used. The volume ratio between organic solvent and aqueous solution preferably is from about 1:3 to about 1:8. Subsequently, all of the supernatant organic phase or an aliquot portion thereof, is separated in a conventional manner from the aqueous phase and any solids therein. For example, the mixture may be cooled to a temperature below the freezing point of the aqueous solution and the liquid organic phase be poured from the solid frozen aqueous phase, or only an aliquot portion of the supernatant organic phase may be recovered by means of pipetting.

Finally, a steroid-containing residue is recovered from the organic extract and is then subjected to a conventional radioimmunoassay test for determining the amount of the steroid therein.

The recovery of steroid-containing residue, which is suitable for a radioimmunoassay determination of the amount of a steroid therein, comprises evaporating the organic solvent therefrom and optionally further purification of the raw evaporation residue, by conventional chromatographic methods, in order to eliminate components therein which will interfere with the radioimmunoassay test. Whether and to what extent a further purification of the initial evaporation residue is necessary will depend on the selectivity (specificity) of the antiserum which is available for the steroid which is to be determined.

In the case of 17α-hydroxy-progesterone, for which a highly selective antiserum is available, it has been found that a simple ether extraction of the aqueous eluate of the dried blood sample is sufficient to eliminate any blood components which might interfere with the radioimmunoassay, and subsequent evaporation of the ether from the extract is sufficient to obtain a residue which can be directly subjected to the radioimmunoassay. The conventional separation of the plasma from the hematocrit (=mass of the blood cells) of the blood sample is omitted in the method according to the present invention, as no interference from hematocrit components, e.g., from erythrocytes, is observed in the radioimmunoassay determination of the steroid. Further, it has been established that standard size of absorbing sheet contains standard amount of serum or whole blood.

Radioimmunoassay techniques for the determination of the various steroid hormones are well known in the art. The steroid-containing residues from body liquids, e.g., blood samples, which have been treated according to the present invention, can be tested in any of these conventional radioimmunoassay tests in the same manner as steroid fractions which have been recovered from body liquids, in particular blood plasma in a conventional way.

For example, to determine the 17α-hydroxy-progesterone content of a blood sample according to the present invention, the residue is preferably obtained by the evaporation of the ether from the ether extract from an aqueous eluate of an absorbing paper, containing the dried blood sample. The residue is then preferably redissolved in an, eluant, being preferably an aqueous solution, having a pH-value of from about 6 to about 8, e.g., a sodium monophosphate/sodium diphosphate buffer solution. For instance, a 0.01 M phosphate buffer solution, containing 0.1% of gelatin and 0.01% of sodium azide is suitable as eluant.

A sufficient solution of a known amount of radioisotopically labeled 17α-hydroxy-progesterone, e.g., 1,2-$^3$H-17α-hydroxy-progesterone, in the same buffer solution and a sufficient solution of an amount of the antiserum for 17α-hydroxy-progesterone in the same buffer solution is then added to bind an important portion, preferably between about 30 and about 50% of the radioisotopically labeled 17α-hydroxy-progesterone.

In order to allow the formation of the steroid-antibody-adduct, the mixture is incubated at about ambient temperature for a period of about ½-2 hours and subsequently at ice bath temperature for a further period of about 15 to 30 minutes. Subsequently, the free steroids are separated from the steroid-antibody-adduct in a conventional manner, preferably by means of charcoal adsorption, and the radioactivity of the remaining steroid-antibody-adduct solution is determined.

Finally, in another embodiment of the invention, there is provided a means for the determination of a steroid hormone in a sample of a human body liquid, comprising a first container, having therein
  (a) an absorbing paper, adapted for absorbing a sample of the human body liquid;
  (b) a second container, containing a first reagent, which comprises a radioistopically labeled form of the steroid hormone; and
  (c) a third container, containing a second reagent, comprising an antiserum for the steroid hormone.

In order to more fully describe the present invention, the method for determining the blood levels of 17α-hydroxy-progesterone utilizing the present invention is described below. It is understood that the specific procedure is intended merely to be illustrative and in no sense limiting.

The 17α-hydroxy-progesterone content in various samples of cord blood and of capillary blood of newborn infants is determined by the method according to the present invention, using blood eluation from filter paper and in a conventional manner by using the plasma-fraction of the blood.

EXAMPLE 1

Specimen of mixed cord blood (=mixture of aterial and venous cord blood) of 33 infants are analyzed. The 17α-hydroxy-progesterone content is determined by radioimmunoassay in samples of the whole cord blood according to the method of the present invention and in samples of the plasma from the same whole cord blood.

Since whole cord blood is comprised of about 50% of serum (or plasma) and 50% of cell mass, 2.5 μl samples of the plasma and 5 μl samples of the whole blood which is equivalent to 2.5 ul of plasma are used.

In order to calculate the exact amount of serum in a 5 μl sample of each of the whole blood specimen two different methods were used; (1) the hematocrit value of the blood specimen (=% by volume of cell mass relative to the total volume of the whole blood) was determined in a conventional manner by separating the serum from the cell mass of whole blood by centrifugation in a hematocrit centrifuge, (2) comparing hormone concentration of plasma samples to that of dried whole blood on filter paper (5 μl whole blood or 3 mm disc size).

1. Preparation of the whole blood sample for the radioimmunoassay to validate the method:
  (a) 5 μl of the blood is pipetted onto a piece of filter paper No. 903 of Schleicher and Schuell, or filter paper used for screening for phenyketonurea:
  (b) a drop of unknown volume of the same blood is put onto a second piece of the same filter paper;
  (c) after the blood has dried, the entire blood-impregnated area of the piece of filter paper, which has been impregnated with 5 μl blood sample, is cut out and dropped into an extraction tube and a disc of 3 mm diameter from the blod impregnated area of the second filter paper piece is punched directly into another extraction tube by means of a paper puncher;
  (d) 500 μl of a 0.01 M sodium monophosphate/sodium/diphosphate buffer solution, containing 0.1% of gelatin and 0.01% of sodium azide (=assay buffer solution) or distilled water is added to each of the extraction tubes. The tubes are then allowed to stand at room temperature for 15 minutes;
  (e) subsequently 3 or 6 milliter of ether is added to each tube and the tubes are vigorously shaken by means of a vortex vibrator or shaker;
  (f) an aliquot of the supernatant liquid organic phase is pipetted out of extraction tube and transferred in the culture tube at room temperature the ether in the culture tube is evaporated under the filtered air in warm water bath (at 37° C.). The resulting residue is directly subjected to the radioimmunoassay test.

2. Preparation of the comparative plasma sample for the radioimmunoassay: The plasma is separated from the whole blood in a conventional hematocrit centrifuge and is diluted with the assay buffer solution or distilled water. An amount of the plasma-dilution, which is equivalent to 2.5 µl of plasma, is pipetted into an extraction tube and the volume of the plasma-dilution is brought up to 500 µl with the above buffer solution or distilled water and the plasma dilution is then treated as described in the foregoing steps 1 f and 1 g. The resulting residue is directly subjected to the radioimmunoassay test.

3. Radioimmunoassay:

Reactants:

Antiserum for 17α-hydroxy-progesterone: an antiserum to 17α-hydroxy-progesterone conjugated at position 17, which is raised in rabbits, is used. A final dilution of the antibody in the assay solution of 1:3000 is used in an amount sufficient for binding 42% of the radiolabeled 17α-hydroxy-progesterone.

Radiolabeled 1,2-$^3$H-17α-hydroxy-progesterone (specific activity 40 ci/mM) obtained from New England Nuclear. A solution of the radiolabeled steroid in the assay buffer solution equivalent to 5000 dpm is used in each test.

Plasma blanks, containing no detectable amounts of 17α-hydroxy-progesterone, are obtained by treating plasma with dextran-coating charcoal (stripped plasma).

Whole blood blanks dried on filter paper or whole blood itself, containing no detectable amounts of 17α-hydroxy-progesterone, are obtained from prepubertal patients with Addison's disease.

All blanks are extracted as described above (1c–1f).

Test procedure:

To each residue, 0.1 ml of the working solution of the radiolabeled 17α-hydroxy-progesterone in assay buffer solution and 0.1 ml of the working solution of the antiserum in assay buffer solution are added. The mixture is incubated at room temperature for 1½ hours and then placed in an ice bath for 15 to 30 minutes. Subsequently, 1 ml of charcoal dextran (=a suspension of 100 mg T70 dextran and 1 g of charcoal A in 400 ml of the assay buffer solution, stored at 4° C.), is added to the mixture in the cold (at 4° C. temperature). The mixture is briefly vortexted, incubated for 10 minutes and centrifuged in the cold (at 4° C.) at 3000 rpm for 10 minutes. The supernatant is decanted into a counting vial with 10 ml of a toluene liquid scintillant and shaken for 1 hour and then counted for $^3$H activity.

A standard curve is prepared with standard solutions, containing between 0 and 1000 pg of unlablled 17α-hydroxy-progesterone.

The results (mean values of triplicate samples) are given in Table I below.

As can be seen from the hematocrit values, the amount of plasma in 5 µl of whole blood is approximately equal to 2.5 µl of plasma. The concentration of 17α-hydroxy-progesterone, which was detected in 2.5 µl of plasma is similar to that which was found in 5 µl of whole blood, dried on the filter paper. This indicates that the recovery of 17α-hydroxy-progesterone from the filter paper is substantially complete. This also suggests that 17α-hydroxy-progesterone is found only in the plasma phase of the blood.

Evaluation of the assay:

The lower limit of sensitivity of the assay is 5 pg/test tube. The intra-assay and inter-assay coefficient of variation for the whole blood samples dried on filter paper does not exceed 13% and 17% respectively.

In control samples, which are obtained by adding various amounts of 17α-hydroxy-progesterone in the range from 0–500 pg per test tube to plasma blanks and to whole blood banks, the recovery of unlabeled 17α-hydroxy-progesterone is between 87 and 104%. The recovery of radioisotopically labeled 17α-hydroxy-progesterone is between 90 and 106%.

To test the effect of time (days) and temparature, samples of dried cord blood on filter paper were stored at room temperature for about a month.

The concentration of 17α-hydroxy-progesterone in discs of filter paper of these cord blood samples was determined as described above. The concentration of 17α-hydroxy-progesterone was found to be substantially the same in discs often having been stored for various periods of time for up to 32 days.

EXAMPLE 2

Samples of capillary blood of neonatal normal infants, ranging in age from 3 days to 4 weeks, are collected directly on the filter paper by means of heel prick without quantitation. Two discs of 3 mm diameter of the blood-impregnated paper are punched out for analysis. In addition, plasma samples of 6 normal infant and 79 sick infants with various medical problems other than CAH were analysed. The 17α-hydroxy-progesterone concentration is determined as described in Example 1.

The following 17α-hydroxy-progesterone concentrations (calculated as ng/ml of plasma) are found:

| | |
|---|---|
| Normal infants by filter paper samples: | |
| (33 infants) | <1.2–3.6 ng/ml |
| Normal infants by plasma samples: | |
| (6 infants) | 0.7–2.5 ng/ml |
| Sick infants by plasma samples: | |
| (79 infants suffering | |
| from various diseases | |
| other than CAH) | 1–12 ng/ml |

| Infants suffering from CAH | | |
|---|---|---|
| | markedly elevated | |
| | (by filter paper samples) | (by plasma samples) |
| 1. Infant age 2 days | 130 ng/ml | 150 ng/ml |
| 2. Infant$^x$ age 4 days | 165 ng/ml | 150 ng/ml |
| 3. Infant$^x$ age 7 days | 65 ng/ml | 68 ng/ml |
| 4. Infant$^x$ age 2 weeks | 335 ng/ml | 310 ng/ml |
| 5. Infant$^x$ age 4 weeks | 360 ng/ml | 390 ng/ml |

$^x$In follow-up samples, taken after several days of treatment with glucocorticoid, the 17α-hydroxyprogesterone concentration in the normal range is found.

TABLE I

| Blood Specimen No. | % Hematocrit | p g 17α-hydroxy-progesterone /sample in | | | Calculated 1 blood per disc[x] | Calculated 17 α-hydroxy-progesterone concentration in the plasma (ng/ml) | | |
|---|---|---|---|---|---|---|---|---|
| | | 2,5 μl of plasma | 5 μl of blood on filter paper | blood on filter paper disc 30 mm φ | | in the plasma sample | in the 5 μl blood sample on paper | in the blood on paper disc[xx] 3 mm φ |
| 1 | 50 | 90 | 86 | 53 | 3.1 | 36 | 34 | 30 |
| 2 | 53 | 43 | 42 | 31 | 3.7 | 17 | 17.8 | 17 |
| 3 | 53 | 142 | 141 | 112 | 3.9 | 57 | 59 | 63 |
| 4 | 50 | 110 | 109 | 67 | 3.1 | 44 | 43 | 38 |
| 5 | 53 | 46 | 37 | 28 | 3.8 | 18 | 16 | 16 |
| 6 | 49 | 110 | 125 | 80 | 3.2 | 44 | 49 | 45 |
| 7 | 54 | 146 | 106 | 74 | 3.4 | 58 | 46 | 42 |
| 8 | 50 | 107 | 93 | 50 | 2.6 | 42 | 37 | 29 |
| 9 | 44 | 115 | 105 | 66 | 3.1 | 46 | 38 | 38 |
| 10 | 50 | 113 | 73 | 63 | 4.3 | 45 | 29 | 36 |
| 11 | 65 | 73 | 52 | 41 | 3.9 | 29 | 29 | 24 |
| 12 | 48 | 134 | 144 | 79 | 2.7 | 54 | 55 | 45 |
| 13 | 45 | 93 | 990 | 67 | 3.7 | 37 | 33 | 38 |
| 14 | 60 | 75 | 55 | 45 | 4.1 | 30 | 27 | 26 |
| 15 | 49 | 159 | 153 | 106 | 3.4 | 63 | 60 | 60 |
| 16 | 58 | 142 | 114 | 88 | 3.8 | 57 | 54 | 50 |
| 17 | 53 | 67 | 73 | 60 | 4.1 | 30 | 31 | 34 |
| 18 | 53 | 91 | 84 | 75 | 4.4 | 36 | 36 | 42 |
| 19 | 50 | 67 | 77 | 61 | 3.9 | 26 | 31 | 34 |
| 20 | 39 | 51 | 45 | 36 | 3.9 | 20 | 15 | 20 |
| 21 | 52 | 43 | 30 | 28 | 4.7 | 17 | 13 | 16 |
| 22 | 56 | 148 | 147 | 104 | 3.5 | 60 | 66 | 60 |
| 23 | 43 | 87 | 106 | 77 | 3.7 | 35 | 36 | 43 |
| 24 | 47 | 79 | 93 | 64 | 3.4 | 32 | 35 | 36 |
| 25 | 67 | 151 | 103 | 74 | 3.5 | 60 | 62 | 42 |
| 26 | 52 | 141 | 151 | 108 | 3.5 | 56 | 64 | 61 |
| 27 | 37 | 75 | 75 | 58 | 3.8 | 30 | 24 | 32 |
| 28 | 45 | 96 | 80 | 57 | 3.4 | 38 | 30 | 32 |
| 29 | 52 | 146 | 134 | 79 | 2.9 | 58 | 56 | 45 |
| 30 | 67 | 156 | 111 | 80 | 3.6 | 62 | 67 | 45 |
| 31 | 45 | 100 | 111 | 76 | 3.4 | 40 | 41 | 43 |
| 32 | 46 | 110 | 105 | 62 | 2.9 | 43 | 37 | 35 |
| 33 | 53 | 78 | 80 | 52 | 3.2 | 31 | 34 | 30 |
| Mean | 50.8 | 102 | 95 | 66 | 3.56 | 40.9 | 39.7 | 37.8 |
| ± SD | 6.9 | 35 | 33 | 22 | .48 | 14.0 | 15.1 | 12.0 |
| Correlation Coefficient[xxx] | | | 9.881 | | | | 0.941 | 0.860 |

[x] calculated by comparing the amount of steroid in blood in the disc with that in the 5 μl blood on the filter paper.
[xx] based on average hematocrit value of 50.8% and average volume of blood on the disc of 3.56 μl/disc.
[xxx] between plasma samples and whole blood samples on filter paper.

What is claimed:

1. A method for determination of a steroid contained in a sample of a human body liquid which comprises the steps of:
    (a) transferring said liquid sample onto a sheet of material which is capable of uniformly absorbing said liquid sample;
    (b) drying the sample-containing sheet;
    (c) treating a portion of the dry sample-containing sheet, which is equivalent to a predetermined amount of the sample, with an aqueous solvent in order to obtain a mixture wherein the dried sample of human body liquid is substantially redissolved in the aqueous solvent;
    (d) extracting said aqueous mixture with a volatile organic solvent capable of dissolving said steroid in order to obtain an organic extract containing said steroid dissolved therein;
    (e) separating at least a portion of said organic extract from said aqueous mixture;
    (f) recovering a residue containing the steroid from said organic extract;
    (g) contacting said residue with an aqueous solution of an agent, said agent being capable of selectively binding said steroid, in the presence of a radioisotopically labeled form of the steroid, whereby part of said labeled steroid and part of said unlabeled steroid present in the sample, are bound by forming a complex with said binding agent, separating said bound steroids from unbound steroids in said aqueous solution and measuring the radioactivity of at least said separated binding agent-steroids-complex or said unbound steroids to determine the concentration of said hormone as a function of the measured radioactivity.

2. The method as defined in claim 1, wherein the steroid-binding agent is a steroid-antiserum.

3. The method as defined in claim 1, wherein the steroid is a steroid hormone selected from the group consisting of adrenal and gonadal sex steroids and corticosteroids.

4. The method as defined in claim 3, wherein the steroid is selected from the group consisting of 17α-hydroxy-progesterone, androstenedione, testosterone, dehydroepiandrosterone, dehydroepiandrosterone-sulfate and cortisol.

5. The method as defined in claim 1, wherein said sample of human body liquid is a sample of whole blood.

6. The method as defined in claim 5, wherein the steroid is 17α-hydroxy-progesterone.

7. The method as defined in claim 6, wherein the organic solvent is a non-water-miscible solvent, step (e) essentially consists of evaporating the organic solvent from the organic extract, whereby the 17α-hydroxy-progesterone-containing residue is obtained, and step (g) comprises of steps of:
- (h) adding to the 17α-hydroxy-progesterone containing residue an aqueous solution containing a predetermined amount of an antiserum for 17α-hydroxy-progesterone and an aqueous solution containing a predetermined amount of a radio-isotopically labeled form of 17α-hydroxy-progesterone, which is in excess of the amount which is required to bind said amount of antiserum;
- (i) allowing a steroid-radioactive steroid-antiserum adduct to form in the aqueous solution;
- (j) separating the unbound steroids from the aqueous solution of (t); and
- (k) determining the content of radioactivity of radio-isotopically labeled steroid in the aqueous solution.

8. The method as defined in claim 7, wherein said radioisotopically labeled 17α-hydroxy-progesterone is labeled with $^3H$.

9. The method as defined in claim 8, wherein said blood sample is of a newborn infant, suspected of being affected by congenital adrenal hyperplasia and whereby the results of that method provide a determination of the condition (diagnosis and therapeutic responsiveness virus) of congenital adrenal hyperplasia for any age group of the patient.

10. The method as defined in claim 7, wherein said blood is utilized in an amount of from about 5 to about 20 μl for the diagnosis of congenital adrenal hyperplasia.

11. The method as defined in claim 7, wherein the organic solvent is ether.

12. A method for detecting functional disorders in the human body, which result in an increased level of at least one steroid hormone in a human body liquid, which comprises the steps of subjecting a sample of the human body liquid to the method as defined in claim 1.

13. A method for detecting congenital adrenal hyperplasia in newborn infants, which comprises the steps of collecting a blood sample of the newborn infant on a sheet of absorbing material and subjecting this blood sample to the method as defined in claim 7.

14. The method as defined by claim 1, further comprising, after drying the sample-containing sheet, the step of storing the dried sheet for an extended period of time up to about 1 month at ambient temperature.

15. A combination for the determination of a steroid hormone in a sample of a human body liquid, comprising:
- (a) a first container having therein an absorbing paper adapted for absorbing the sample of the body liquid;
- (b) a second container, containing a first reagent which comprises a radioisotopically labeled form of the steroid hormone; and
- (c) a third container, containing a second reagent comprising an antiserum for the steroid hormone.

16. The combination, as defined in claim 15, wherein the steroid hormone is 17α-hydroxy-progesterone.

* * * * *